(12) United States Patent
Kurosawa et al.

(10) Patent No.: US 8,517,959 B2
(45) Date of Patent: Aug. 27, 2013

(54) GUIDE WIRE FOR MEDICAL TREATMENT

(75) Inventors: Tomokane Kurosawa, Fuji (JP); Yutaka Tano, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/270,601

(22) Filed: Oct. 11, 2011

(65) Prior Publication Data
US 2012/0029478 A1    Feb. 2, 2012

Related U.S. Application Data

(63) Continuation of application No. PCT/JP2010/056600, filed on Apr. 13, 2010.

(30) Foreign Application Priority Data

Apr. 14, 2009 (JP) ................................ 2009-098463

(51) Int. Cl.
*A61M 25/00* (2006.01)
*A61M 25/01* (2006.01)
*A61M 25/09* (2006.01)

(52) U.S. Cl.
USPC ........... 600/585; 600/434; 604/528; 604/530; 604/532

(58) Field of Classification Search
USPC .................. 600/585, 434; 604/528, 530, 532
See application file for complete search history.

(56) References Cited

U.S. PATENT DOCUMENTS

| | | | | |
|---|---|---|---|---|
| 4,898,591 A | * | 2/1990 | Jang et al. | 604/527 |
| 4,950,228 A | * | 8/1990 | Knapp et al. | 604/8 |
| 5,295,493 A | | 3/1994 | Radisch, Jr. | |
| 5,427,119 A | * | 6/1995 | Swartz et al. | 600/585 |
| 5,445,625 A | * | 8/1995 | Voda | 604/532 |
| 5,575,766 A | * | 11/1996 | Swartz et al. | 604/508 |

(Continued)

FOREIGN PATENT DOCUMENTS

| | | |
|---|---|---|
| EP | 1 920 795 A1 | 5/2008 |
| JP | 07-255856 A | 10/1995 |

(Continued)

OTHER PUBLICATIONS

International Search Report (PCT/ISA/210) issued on Jul. 13, 2010, by Japanese Patent Office as the International Searching Authority for International Application No. PCT/JP2010/056600.

(Continued)

*Primary Examiner* — Sean Dougherty
(74) *Attorney, Agent, or Firm* — Buchanan Ingersoll & Rooney PC

(57) ABSTRACT

A guide wire for medical treatment includes a straight-line shaped proximal section and a distal section which is continuous with the distal side of the proximal section and whose most distal portion faces toward the proximal direction. The distal section includes a curved portion continuous with the proximal section and a distal portion continuous with the distal side of the curved portion, the proximal section and at least a portion on the proximal side of the curved portion continuous with the proximal section are positioned on an identical plane, and the distal portion is extended toward a direction backing away from the plane and includes the most distal portion in a section of a direction to which the curved portion is curved with respect to an plane n an axis core of the proximal section orthogonal to the plane.

21 Claims, 13 Drawing Sheets

(56) References Cited

U.S. PATENT DOCUMENTS

| | | | |
|---|---|---|---|
| 5,722,400 | A | 3/1998 | Ockuly et al. |
| 5,728,148 | A | 3/1998 | Bostrom et al. |
| 5,807,339 | A | 9/1998 | Bostrom et al. |
| 5,879,296 | A * | 3/1999 | Ockuly et al. ............. 600/374 |
| 6,083,213 | A * | 7/2000 | Voda ............................ 604/500 |
| 6,203,531 | B1 * | 3/2001 | Ockuly et al. ............. 604/264 |
| 6,214,016 | B1 | 4/2001 | Williams et al. |
| 6,254,550 | B1 | 7/2001 | McNamara et al. |
| 6,475,195 | B1 * | 11/2002 | Voda ............................ 604/264 |
| 6,558,368 | B1 * | 5/2003 | Voda ............................ 604/532 |
| 7,048,695 | B1 | 5/2006 | Schwager |
| 7,248,913 | B2 * | 7/2007 | Hassett ........................ 600/374 |
| 7,875,018 | B2 * | 1/2011 | Tockman et al. ............ 604/510 |
| 7,942,832 | B2 | 5/2011 | Kanuka et al. |
| 2002/0032391 | A1 | 3/2002 | McFann et al. |
| 2008/0306468 | A1 | 12/2008 | Tamai et al. |
| 2009/0105724 | A1 | 4/2009 | Yoshizaki et al. |
| 2009/0287135 | A1 | 11/2009 | Michishita et al. |

FOREIGN PATENT DOCUMENTS

| | | |
|---|---|---|
| JP | 8-252262 A | 10/1996 |
| JP | 11-076415 A | 3/1999 |
| JP | 2004-154286 A | 6/2004 |
| JP | 2004-181184 A | 7/2004 |
| JP | 2004-222880 A | 8/2004 |
| JP | 2006-025907 A | 2/2006 |
| JP | 2006-141778 A | 6/2006 |
| JP | 2006-230482 A | 9/2006 |
| JP | 2007-61181 A | 3/2007 |
| JP | 2008-125628 A | 6/2008 |
| WO | WO 00/53250 A1 | 9/2000 |
| WO | 03/089039 A1 | 10/2003 |

OTHER PUBLICATIONS

Extended European Search Report issued Sep. 4, 2012 by the European Patent Office in European Patent Application No. 10 764 451.0.

* cited by examiner

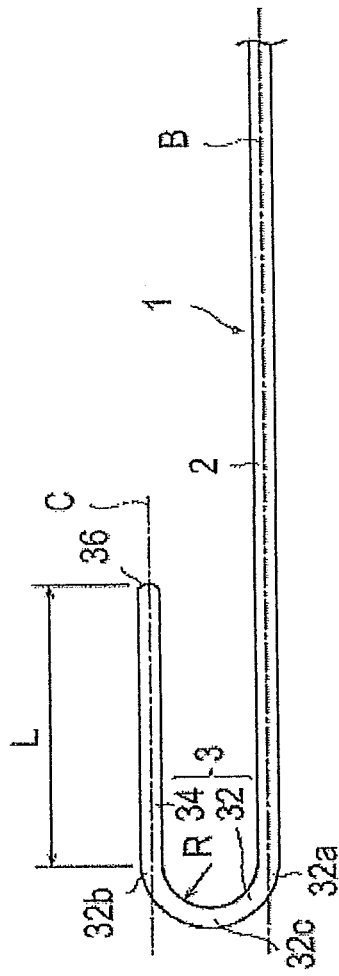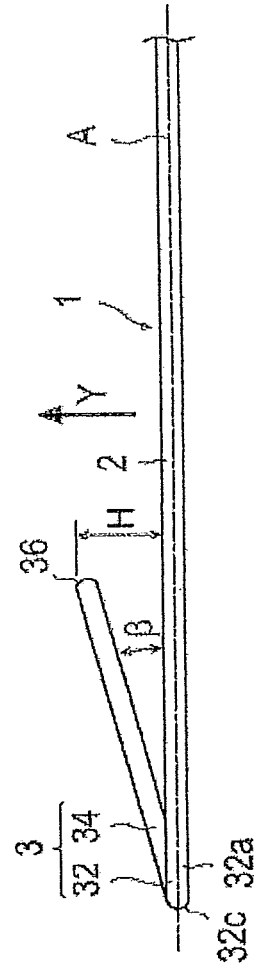
Fig. 1A
Fig. 1B

GUIDE WIRE FOR MEDICAL TREATMENT

This application is a continuation of International Application No. PCT/JP2010/056600 filed on Apr. 13, 2010, and claims priority to Japanese Application No. 2009-098463 filed on Apr. 14, 2009, the entire content of both of which is incorporated herein by reference.

TECHNOLOGICAL FIELD

The present invention relates to a guide wire for medical treatment used for introducing a medical device such as a catheter and the like to a desired region inside a blood vessel.

BACKGROUND DISCUSSION

A guide wire for medical treatment is used for introducing and indwelling a medical tool such as a catheter and an introducer kit inside a blood vessel when carrying out diagnosis and treatment of a blood vessel percutaneously. In the past, the predominant thinking was that the region for introducing a medical device such as a catheter into a blood vessel is a femoral region (FEMORAL-REGION). But in order to reduce the burden on the patient, there has been a trend in recent years to shifting to a brachial region (BRACHIAL-REGION) and, in particular, to a radial region (RADIAL-REGION). There has been a desire for a guide wire for medical treatment which can be used safely inside an arm blood vessel that often includes a branch and/or a meandering configuration and also, and which exhibits excellent operability.

In the past, there has been used a guide wire for medical treatment having a J-shape at the distal end thereof when carrying it from a radial region (RADIAL-REGION) to a target region in the vicinity of the heart. In this case, insertion is carried out into the blood vessel by setting the J-shape of the distal end upright, but when the guide wire is further pushed ahead in a state in which the J-shape of the distal end reaches a side-branch of the blood vessel, the guide wire deviates from the aimed blood vessel and is pushed-ahead toward the side-branch. In this case, the operation was complicated such that the operator must pull out the guide wire from the side-branch once and thereafter, must push it forward again by aiming the objective blood vessel. Further, whether or not the guide wire moves erroneously into the side-branch is confirmed usually by using an X-ray contrast and the operator has to inject the contrast agent to the patient in each case thereof, so that there was a fear of physical influence with respect to the patient.

To address this, Japanese Unexamined Application Publication No. 2004-181184 discloses a guide wire constructed to prevent it from going erroneously into a branch of a blood vessel by setting the angle formed between an extended line of a distal straight line portion of a J-shaped guide wire and a wire base to be 40° to 70°.

However, in case of carrying a guide wire from a radial region (RADIAL-REGION) to a heart, the guide wire must be advanced through a blood vessel path having a lot of branched blood vessels compared with a femoral region (FEMORAL-REGION) or a brachial region (BRACHIAL-REGION). Even employing a J-shaped guide wire whose distal end is formed by a certain angle, it is not able to avoid the guide wire from moving erroneously into a branched blood vessel, and there has been required a guide wire which can be carried reliably until a target region in the vicinity of the heart. Moreover, even if there is a case in which the J-shape of the distal end goes straight ahead after returning to the original J-shape caused by inversion in a state of getting into the branched blood vessel, there might occur a case in which the guide wire will go erroneously into a different branched blood vessel depending on the distal shape of the guide wire.

SUMMARY

A guide wire for medical treatment disclosed here includes a straight-line shaped proximal section, and a distal section continuous with a distal end of the proximal section so that a distal-most portion of the distal section faces in a proximal direction. The distal section includes a curved portion continuous with the proximal section and a distal portion continuous with a distal end of the curved portion, wherein the proximal section and at least a proximal portion of the curved portion which is continuous with the proximal section are positioned on a common first plane, with the distal portion extending toward a direction extending away from the first plane. The distal-most end of the distal portion is positioned on one side of a second plane which is orthogonal to the first plane and in which the proximal section lies, and at least a distal portion of the curved portion is positioned on the one side of the second plane. The guide wire exhibits improved operability and safety, and reduces the burden on the operator.

The guide wire configured in the manner described above can take on a three dimensional structure in which the distal portion is extended in a direction moving away from the plane so that it is possible to be formed in a spiral shape when the distal portion is extended. It is thus possible to carry out a guide wire operation in which the distal portion is not so susceptible to entering a branched blood vessel caused by a driving or forward pushing force transmission mechanism specific to the spiral shape thereof. Even in a case in which the distal portion of the guide wire is hooked in the vicinity of an entrance of a branched blood vessel, it is possible to distribute the pushing force which is added continuously from the hand (proximal) side, and moreover, it is relatively easy for the distal portion of the guide wire to be disengaged from the branched blood vessel and to decrease a phenomena of the distal portion erroneously entering branched blood vessels.

Also, even in a situation in which the distal-most portion of the guide wire cannot be disengaged from the branched blood vessel, it is possible for the guide wire to return to the shape before extending the distal portion inside the blood vessel (the original shape) by further pushing, so that it is possible to restore a safe shape which is not likely to injure the blood vessel wall. Further, even if pushing the guide wire forward when the distal portion has been returned to its original shape, it is possible for the guide wire to move straight ahead without going into the branched blood vessel.

Also, the most distal portion thereof is provided in a section in a direction, toward which the curved portion is curved, with respect to an plane on an axis of the proximal section orthogonal to the plane, so that after the guide wire returns to the original shape inside the blood vessel, it is possible for the guide wire to return to the spiral shape relatively easily by pulling the guide wire backward after hooking the most distal portion of the guide wire onto the entrance of the branched blood vessel.

According to another aspect, a guide wire for medical treatment comprises a straight proximal section possessing a distal-most end, and a distal section possessing a proximal-most end which is continuous with the distal-most end of the proximal section so that the straight proximal section extends in a proximal direction away from the distal section. The distal section includes a curved portion and a distal portion, with the curved portion being a proximal-most portion of the distal section, and the distal portion being located distally of the curved portion and being a distal-most part of the distal section; and with the curved portion possessing a curve start point at which curving of the curved portion starts and a curve end point at which curving of the curved portion ends, with the curve start point being spaced apart from the curve end point, and wherein the curved portion curves continuously from the curve start point to the curve end point. The proximal section and at least a proximal-most portion of the curved portion are positioned in a common first plane, with the first plane being a horizontal first plane when the straight proximal section is horizontal. The distal portion is oriented so that the axis of the distal portion intersects the first plane, and the distal portion possessing a distal-most end which is a distal-most end of the guide wire, the distal-most end of the distal portion and a distal-most part of the curved portion being located on a common side of a second plane, wherein the second plane is perpendicular to the first plane, and the straight proximal section lies in the second plane, with the second plane being a vertical plane when the straight proximal section is horizontally positioned.

In accordance with another aspect, a guide wire for medical treatment comprises a proximal section possessing a distal-most end and a proximal-most end, wherein the proximal section extends along a straight line from the distal-most end of the proximal section to the proximal-most end of the proximal section; a distal section possessing a proximal-most end which is continuous with the distal-most end of the proximal section so that the proximal section extends in a proximal direction away from the distal section, wherein the distal section includes a curved portion and a distal portion; with the curved portion possessing a proximal-most end that is continuous with the distal-most end of the proximal section, and the curved portion also possessing a distal-most end; and with the distal portion being located distally of the curved portion and possessing a proximal-most end that is continuous with the distal-most end of the curved portion. The distal section possesses a distal-most end that is also a distal-most end of the distal portion and a distal-most end of the guide wire. The curved portion possesses a curve start point at which curving of the curved portion starts, with the curve start point coinciding with the proximal-most end of the curved portion, and the curved portion possessing a curve end point at which curving of the curved portion ends, with the curve end point coinciding with the distal-most end of the curved portion. The curve start point is spaced apart from the curve end point along a length of the curved portion, and the curved portion curves continuously from the curve start point to the curve end point. The proximal section and at least a proximal-most portion of the curved portion are positioned in a common first plane, the distal portion does not lie in the first plane, and distal-most end part of the curved portion and the distal-most end of the distal section are positioned on a common side of a second plane, wherein the proximal section lies in the second plane, and the second plane is perpendicular to the first plane.

BRIEF DESCRIPTION OF DRAWINGS

FIG. 1A is a plan view of a guide wire for medical treatment according to one embodiment disclosed here by way of example.

FIG. 1B is a side view of the guide wire.

DETAILED DESCRIPTION

Figure 2:
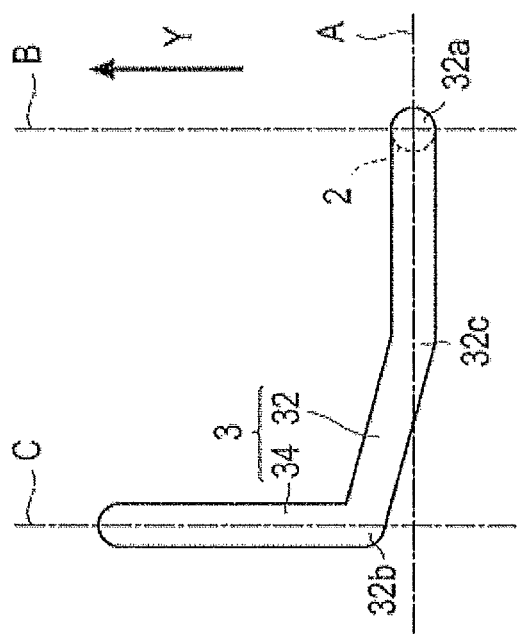
FIG. 2 is an end view of the guide wire seen from the distal end.

Set forth below with reference to the accompanying drawing figures is a description of various embodiments of a guide wire disclosed here. The embodiment of the guide wire are disclosed by way of example. The size ratio in the drawings is exaggerated for convenience of explanation and ease in understanding, and is different from the actual ratio.

A guide wire for medical treatment 1 according to one disclosed embodiment includes, as shown in FIG. 1 and FIG. 2, a straight line-shaped, or linearly extending, proximal section 2 and a distal section 3 positioned on the distal side of the proximal section 2. The linearly extending or straight proximal section 2 possesses a distal-most end that is integrally formed in one piece with the proximal-most end of the distal section 3. The distal section 3 is the end portion on the side inserted into vasculature or a vessel (e.g., a blood vessel, bile duct, ureters). The distal direction refers to a direction toward which insertion is carried out inside the body cavity and the proximal direction refers to the opposite direction. The distal section 3 is made of a metal core composed of a metal material. The metal core possesses a taper shape, though it is also possible to employ a construction in which a taper shape is not employed.

The guide wire 1 is also constructed such that a synthetic resin layer is coated on the metal core composed of a metal material. Examples of materials which can preferably be used for the metal core include a superelastic alloy such as a Ni—Ti alloy, a stainless steel alloy or the like. The material constituting the metal core can be one kind of material or a combination of two or more materials. Also, in order to obtain flexibility at the distal end, the metal core at the distal portion is diameter-reduced in a taper shape. Examples of resin materials which can preferably be used for the synthetic resin layer include a polyurethane, a fluorine-based resin such as PTFE (polytetrafluoroethylene), a polyamide-based resin such as nylon, or polyolefin such as polyethylene and polypropylene. It is possible for those resins to be mixed with X-ray contrast fine particles such as of barium oxide, tungsten and the like. Also, by providing a coil of platinum, gold or the like for X-ray contrast at the distal portion of the core metal, it is also possible to provide a construction in which work (procedures) can be carried out under X-ray fluoroscopy. It is preferable for the surface of the synthetic resin layer to be coated further with a hydrophilic lubricant coating composed of maleic anhydride or the like. Thus, insertion resistance inside a tube for medical treatment such as a catheter and inside a body cavity is reduced, and a smooth insertion therein becomes possible. It is preferable for the lubricant coating not to be coated on a portion which is not inserted into the body cavity. That is, the portion of the guide wire which is intended to remain outside the body cavity preferably is not coated with the lubricant coating.

The outer diameter of such a guide wire 1 is normally around 0.1 mm to 1.40 mm, though is not limited by these values. Further, the full length of the guide wire 1 is around 100 cm to 450 cm, preferably around 120 cm to 350 cm, but the guide wire is not limited to these values.

The distal section 3 includes a curved portion 32 which is curved and a distal portion 34 continuous with the curved portion 32 and positioned distally of the curved portion 34. A most distal portion 36 is located at the distal-most end of the distal portion 34. By virtue of the curved shape of the curved portion 32, the guide wire 1 possesses a J-shape such that the distal-most portion 36 does not face or point towards the distal direction, but rather faces or points towards the proximal direction in its original shape (i.e., in the shape in which no load or force is applied to the distal portion of the guide wire). As illustrated in FIGS. 1A, 1b and 2, in its original shape when no external load is applied to the distal section 3 of the guide wire, and before the distal section 3 is inserted into a blood vessel, the distal section 3 of the guide wire is not coil-shaped.

The curved portion 32 includes a curve start point 32a which is the starting point at which the distal section 3 begins to curve, a curve end point 32b which is the ending point at which the curving of the distal section 3 ends, and a curve midpoint 32c which is a midpoint between the curve start point 32a and the curve end point 32b. In the illustrated embodiment, the curved portion curves continuously from the curved start point 32a to the curved end point 32b. The curve start point 32a is positioned proximally of the curve end point 32b and the curve midpoint 32c along the length of the distal section, while the curve end point 32b is positioned distally of the curve start point 32a and the curve midpoint 32c along the length of the distal section. With respect to the curved portion 32, a portion from the curve start point 32a to the curve midpoint 32c is curved on or lies in a common plane A (first plane), and in this plane A there also lies the proximal section 2. The region from the curve midpoint 32c to the curve end point 32b of the curved portion 32 extends so as to gradually curve out of the plane A while approaching the distal portion 34.

The distal portion 34 gradually extends away from the plane A while approaching the distal-most portion 36. That is, at distances closer to the distal-most portion 36, the distal portion 34 is located farther away from the plane A.

When the proximal section 2 is positioned horizontally as shown in FIG. 1A, the plane A (first plane] is a horizontal plane. The plane B (second plane) shown in FIG. 1B is a plane perpendicular to plane A which contains the proximal section 2 (i.e., the proximal section 2 lies in the plane B). The distal portion 34 is shaped such that the distal-most portion 36 is positioned on the same side of plane B as the curved portion 32. Stated differently and with reference to FIG. 1A, the distal portion 34 is configured so that the distal-most portion 36 and the curved portion 32 are on the same side of the plane B (i.e., the distal-most portion 36 and the curved portion 32 are both on the upper side of plane B in FIG. 1A).

In this embodiment disclosed by way of example, as shown in FIG. 1A, a projection line (axial center) of the distal portion 34 onto the plane A is parallel with the proximal section 2 and the projection line does not intersect the proximal section 2. The distal portion 34 extends in a direction away from the plane A so that an imaginary continuation of the distal portion 34 obliquely intersects the first plane (i.e., forms an oblique angle with the plane A). More specifically, the distal portion 34 does not intersect the plane B.

For a preferable embodiment of the curved portion 32, it is preferable for the radius of curvature R of the curved portion 32 shown in FIG. 1A to be around 0.2 mm to 20 mm, more preferably 0.5 mm to 8 mm, further preferably 1.0 mm to 3.0 mm.

Also, the inclination angle β of both the region from the curve midpoint 32c to the curve end point 32b of the curved portion 32 and the distal portion 34 with respect to the plane A is preferably constant, though it is also possible to employ a configuration in which the inclination angle β is not always constant. In either case, it is preferable that the following relationship is satisfied: −90°<inclination angle β<90°, more preferably −10°<inclination angle β<−40° or 10°<inclination angle β<40°. It should be noted that it is possible for the inclination angle of the curved portion 32 with respect to the plane A and the inclination angle of the distal portion 34 with respect to the plane A to be different.

It is preferable for the height H of the most distal portion 36 from the plane A to satisfy a relation of 0 mm<|H|<20 mm, more preferably 0 mm<|H|<8 mm. It is preferable for the length L of the projection line of the distal portion 34 onto the plane A to be 0.5 mm to 20 mm, more preferably 5 mm to 15 mm.

Figure 12:
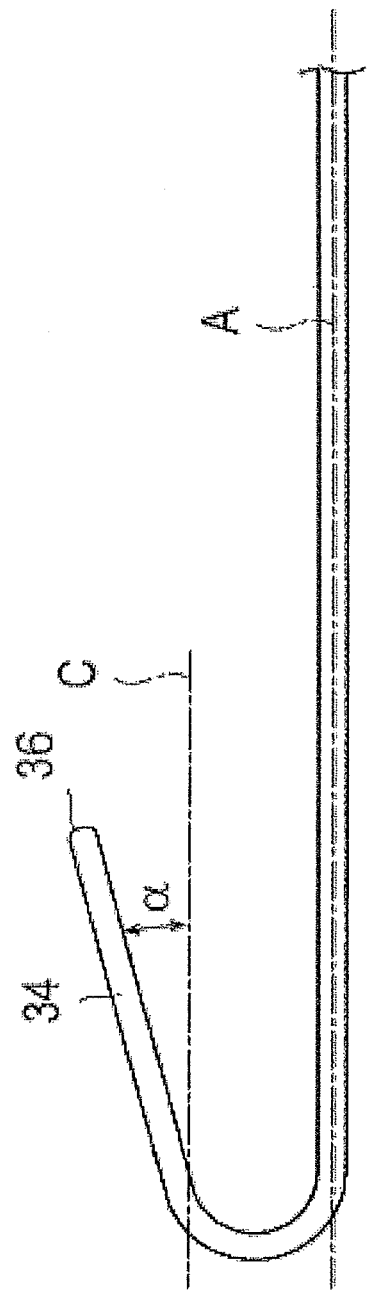
FIG. 12 is a plan view of another modified example of the distal portion of the guide wire for medical treatment.
Figure 13:
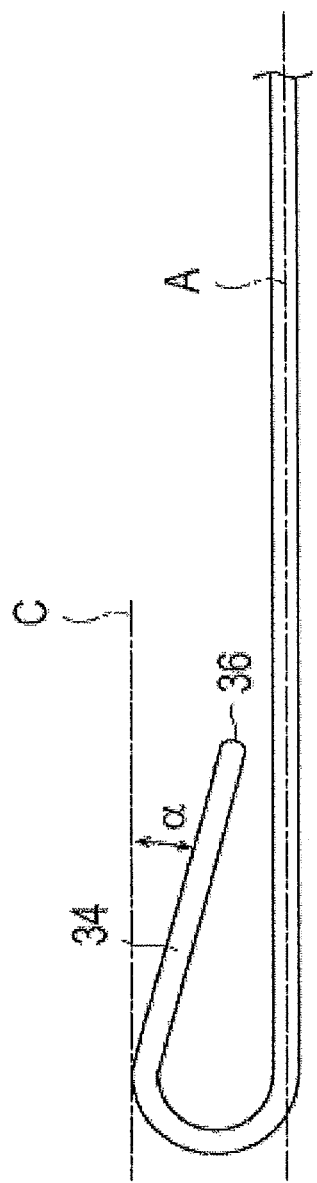
FIG. 13 is a plan view of still another modified example of the distal portion of the guide wire for medical treatment.

Also, the bending angle α of the distal portion 34 with respect to the plane C (the bending angle α is shown in FIG. 12) is 0° in this embodiment, but it is possible to configure the distal portion 34 so that the bending angle α satisfies the following relationship: 0°<bending angle α<90°, more preferably 0°<bending angle α<45° as shown in FIG. 12. It is also possible, as shown in FIG. 13, to configure the guide wire so that the bending angle α<0°, more preferably the bending angle is −45°<α<0°, in a range in which the projection line of the distal portion 34 to the plane A does not intersect the proximal section 2, that is in a range in which the distal portion 34 does not intersect the plane B. In other word, it is also possible to configure the guide wire so that the bending angle is in the noted range in which the most-distal portion 36 is not positioned in the curved portion 32 section of the distal section 3 with respect to plane B.

Set forth below is a description of the operation of the guide wire for medical treatment 1 according to one disclosed use.

Figure 3:
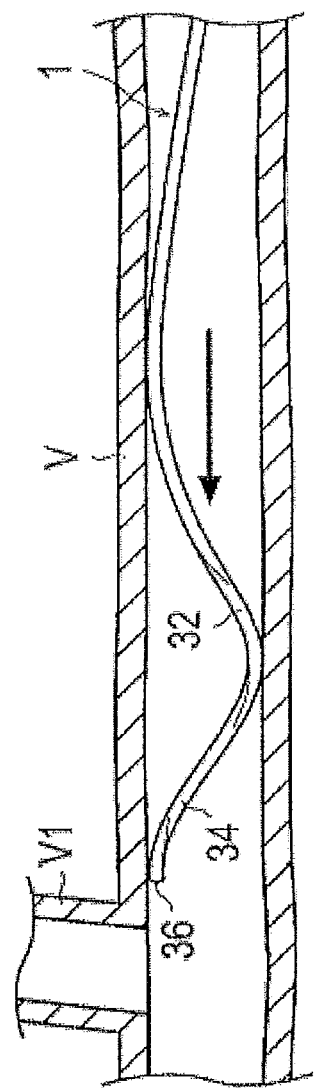
FIG. 3 is a cross-sectional view showing the guide wire inserted into the blood vessel.

Referring to FIG. 3, an operator inserts the distal portion 34 of the guide wire 1 into the blood vessel V. This insertion is carried out by way of a tube-shaped apparatus referred to as an inserter. The guide wire should preferably not be directly inserted into the blood vessel (i.e., without a tube-shaped apparatus/inserter) using the original shape of the guide wire because the original shape of the guide wire has a three-dimensional shape. To insert the guide wire, the operator extends the distal section 3 of the guide wire such that the distal-most portion 36 is directed toward the distal direction (insertion direction). The operator thereafter inserts the extended guide wire into the inserter. At that time, the distal portion 34 is shaped by being extended and is spaced apart from the plane A. A spiral shape is thus formed in the vicinity of the curved portion 32. When insertion into the blood vessel V inside is carried out in this state, as shown in FIG. 3, a portion of the spiral shape contacts the blood vessel wall, so that the shape of the guide wire is generally maintained.

Further, when the operator manipulates or handles the proximal side of the guide wire 1 and continues to push the distal end of the guide wire 1 in the distal or forward direction within the blood vessel V, it sometimes happens that the distal-most portion 36 passes by an entrance of a branched blood vessel V1. By virtue of the guide wire 1 in this embodiment having a spiral-shaped distal end and the distal portion 34 is inclined with respect to the direction of movement of the guide wire 1 while being wound in a spiral circumferential direction, even if the most distal portion 36 contacts the entrance of the branched blood vessel V1, the center axis of the distal portion 34 is deformed so as to be swung laterally such that the spiral pitch will be compressed. The resistive force applied to the blood vessel wall which is a contact point of the entrance of the branched blood vessel V1 is thus distributed. It is thus possible to decrease the phenomena of the guide wire 1 erroneously moving into the branched blood vessel V1. It is also possible to decrease position confirmation operations that involve the use of contrast agents, and so the burden to the patient and the patient's body is lessened and also the expense for the contrast agent is reduced.

Also, in this embodiment disclosed by way of example, the distal side from the curve midpoint 32*c* which is along the curved portion 32 is extended in the original shape so as to back away gradually from the plane A, so that it is relatively easily possible to produce a spiral shape when extended, and it is possible to further heighten an effect for distributing the resistive force applied to the distal section 3. That is, the configuration of the guide wire in FIG. 2 makes it easier to change to the spiral shape when a doctor extends the curved portion 32 for inserting into a inserter or a catheter, and so the distal section can be advanced into a blood vessel as shown in FIG. 3. The shape of the portion of the guide wire on the distal side of the curve midpoint 32*c* is away gradually from the plane A.

Figure 4:
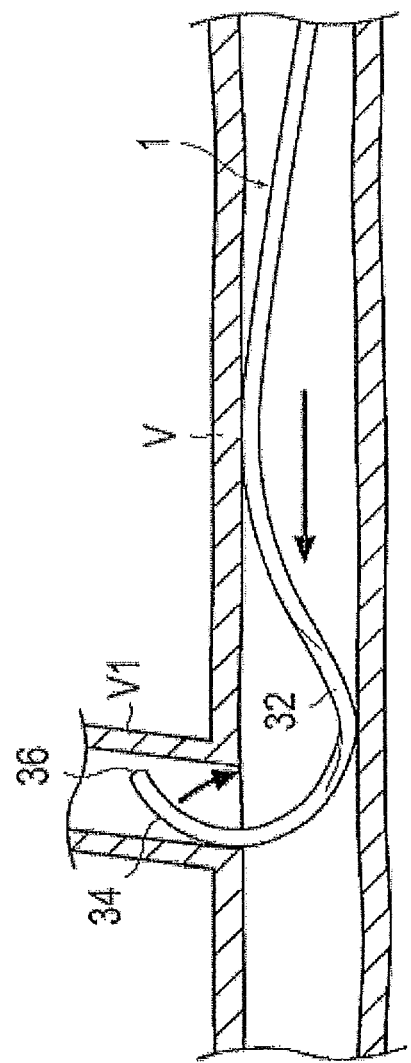
FIG. 4 is a cross-sectional view showing a situation in which the distal portion of the guide wire inserted into the blood vessel is inverted.
Figure 5:
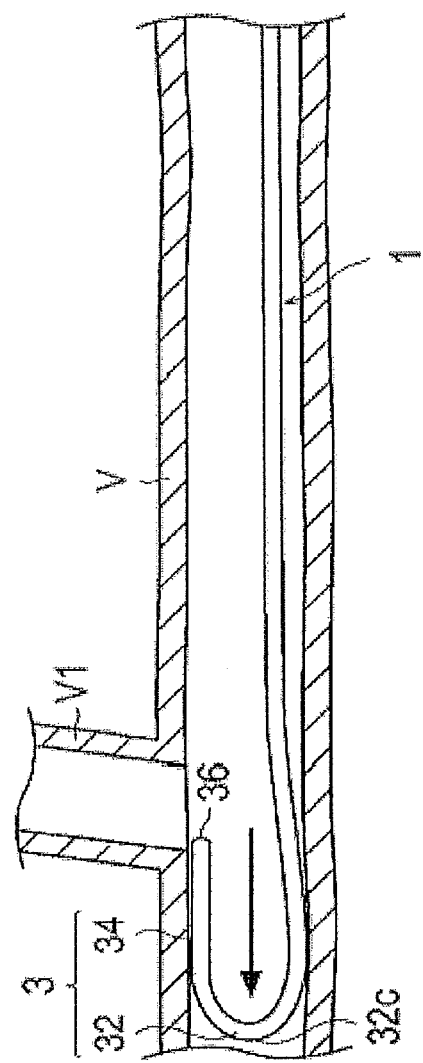
FIG. 5 is a cross-sectional view showing a situation in which the distal portion of the guide wire inserted into the blood vessel returns to its original shape.

Also, as shown in FIG. 4, when the distal-most portion 36 passes by the entrance of the branched blood vessel V1 and the operator pushes it further, the contact of the blood vessel wall and the distal portion 34 becomes a start for bending, and the distal portion 34 of the guide wire 1 is turned around so that distal-most portion 36 is directed toward or faces the proximal direction. As shown in FIG. 5, it becomes possible for the portion 36 to return to the original shape exhibited before the insertion into the blood vessel. Thus, the curved portion 32 of the guide wire 1 becomes the distal-most end in the insertion direction and the guide wire takes on a shape making it difficult for the distal-most portion 36 to contact the blood vessel wall even during a forceful pushing-in of the guide wire by the operator and in which safety is heightened so that damage of the blood vessel wall can be inhibited or prevented. Also, the curve midpoint 32*c* of the curved portion 32, which becomes the distal-most end in the insertion direction, is positioned at the center of the blood vessel diameter, so that it becomes difficult for the curve midpoint 32*c* to contact the blood vessel wall and so it is possible to make the guide wire 1 move straight ahead rather smoothly inside the blood vessel V. In this manner, when the guide wire is in a shape in which it is inserted into the blood vessel V (i.e., the extended shape), the guide wire exhibits properties which inhibit or prevent erroneous entering into the branched blood vessel so that operability is improved. When the distal section 3 is in an inverted shape, there can be further improved safety in a state of maintaining operability. More specifically, it is possible for the guide wire to exhibit properties which inhibit or prevent erroneous entry into the branched blood vessel, and provide quite good operability and safety with excellent balance.

Figure 6:
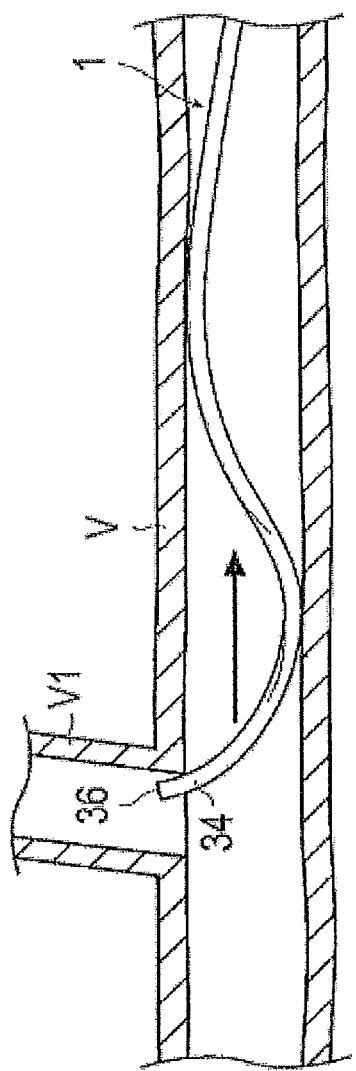
FIG. 6 is a cross-sectional view showing an occasion returning the guide wire for medical treatment, which returned to the original shape inside the blood vessel, to a spiral shape.

Also, in a case in which the distal section 3 of the guide wire 1 is inverted as shown in FIG. 5, the most distal portion 36 faces toward the proximal direction. If it is desired at that time to return the guide wire 1 to the extended shape again, as shown in FIG. 6, it is possible to restore the spiral shape again by hooking the most distal portion 36 of the guide wire 1 at the entrance of the branched blood vessel V1 and thereafter pulling back the guide wire 1 in the backward direction (proximal direction). Thereafter, it is possible to push ahead the guide wire 1 in the forward direction by manipulating or handling the guide wire such that the distal-most portion 36 does not pass by the entrance of the branched blood vessel V1 and while maintaining the spiral shape (i.e., by locating the distal-most portion 36 circumferentially away from the entrance of the branched blood vessel V1, for example diametrically opposite the entrance of the branched blood vessel V1). At that time, the distal portion 34 including the most distal portion 36 is positioned at a section at which the curved portion 32 is curved with respect to the plane B, so that it is possible to restore the spiral shape relatively easily by pulling the guide wire 1 backward. More specifically, in a case in which the most distal portion 36 is positioned on the side of the plane B opposite the side on which the curved portion 32 is located, the projection line of the distal portion 34 onto the plane A intersects the proximal section 2, so that when the most distal portion 36 is hooked and the guide wire 1 is pulled backward, it becomes relatively easy for the distal portion 34 and the proximal section 2 to intersect with each other strongly. That is, it becomes relatively easy to be deformed such that the radius of curvature R of the curved portion 32 becomes smaller, so that it becomes difficult to restore the spiral shape. But in the guide wire disclosed here and illustrated in the drawing figures by way of example, the most distal portion 36 is positioned on the same side of the plane B as the curved portion 32, and the distal portion 34 does not intersect the plane B, so that it is relatively easy for the guide wire 1 to return to the spiral shape.

Figure 7:
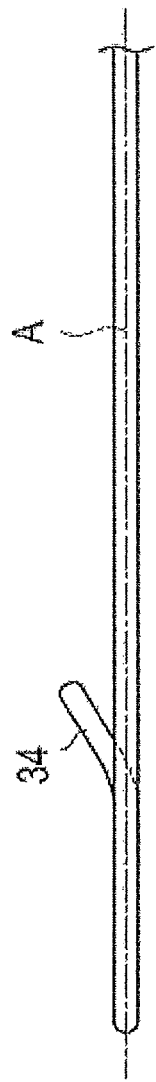
FIG. 7 is a side view showing a modified example of the distal portion of the guide wire for medical treatment.

It should be noted that the guide wire is not limited to the embodiment described above as it is possible to include variations. For example, the configuration of the distal portion 34 is not limited by the configuration shown in FIGS. 1A and 1B, and FIG. 2. As shown in FIG. 7, it is possible for only a portion on the distal side of the distal portion 34 to extend away from the plane A gradually. This configuration includes the curved portion from the curve start point through the curve midpoint to the curve end point which is curved on or lies in the plane A.

Figure 8:
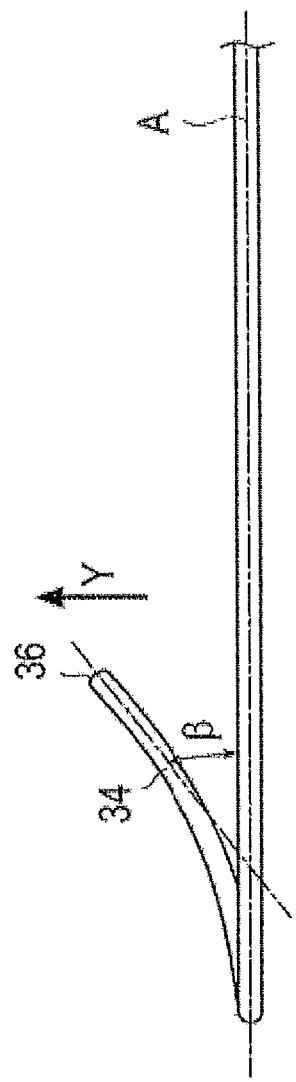
FIG. 8 is a side view showing another modified example of the distal portion of the guide wire for medical treatment.
Figure 9:
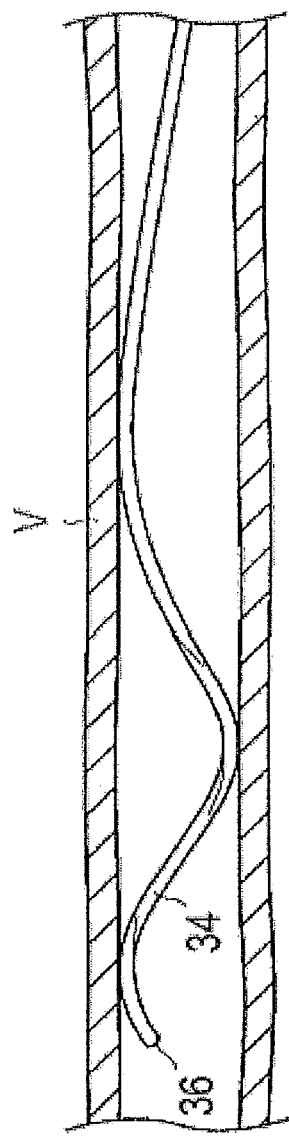
FIG. 9 is a cross-sectional view illustrating insertion of the guide wire shown in FIG. 8 into a blood vessel.

It is also possible to employ a shape which is curved toward the Y direction 36 in which, as shown in FIG. 8, the inclination angle β of the distal portion 34 with respect to the plane A becomes increasingly larger along the length of the distal portion approaching the distal-most end. By employing such a configuration, when inserted into the blood vessel V, as shown in FIG. 9, the distal-most portion 36 does not contact the blood vessel wall by making the region proximally spaced from the distal-most portion 36 contact the blood vessel wall. This helps improve the safety of the guide wire by reducing the possibility that the distal-most portion 36 of the guide wire scratches or bumps the blood the vessel V. It is possible not to employ a construction in which the inclination angle β of the distal portion 34 with respect to the plane A becomes gradually larger approaching the distal-most portion 36, but to instead employ a construction in which the angle becomes larger stepwise by being bent locally or at spaced increments.

It should be noted that it is preferable for the degree of curvature toward the Y direction of the distal portion 34 to be changed appropriately by the guide wire 1. As one example, in order to exert an effect for a subclavian artery having many branched blood vessels, the inner diameter of the average subclavian artery is to be around 6 mm, so that when the guide wire 1 takes on a spiral shape inside the 6 mm inner diameter tube, it is preferable for the most distal portion 36 to be set so as not to contact the inner wall of the tube and so as to be positioned approximately at the center of the inner diameter. By employing a construction in which the most distal portion 36 does not contact the blood vessel wall and further, is positioned approximately at the center of the inner diameter, it is possible to more reliably prevent the guide wire 1 from being inserted erroneously into the branched blood vessel V1 and it is possible to push the guide wire 1 forward relatively smoothly and safely.

Figure 10:
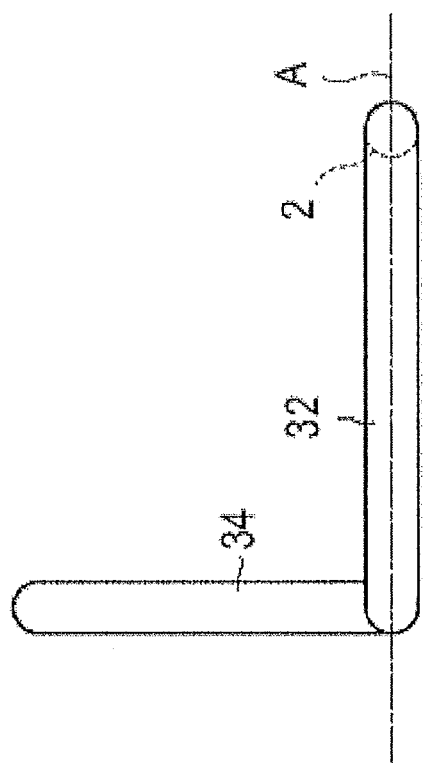
FIG. 10 is an end view of the modified example of the curved portion of the guide wire for medical treatment seen from the distal end.

Also, the configuration of the curved portion 32 is not limited by the configuration shown in FIGS. 1A and B, and FIG. 2 if at least a portion of the proximal side of the curved portion 32 is positioned on the plane A. Therefore, for example, as shown in FIG. 10, it is possible for the whole curved portion 32 to be positioned on the plane A.

Figure 11:
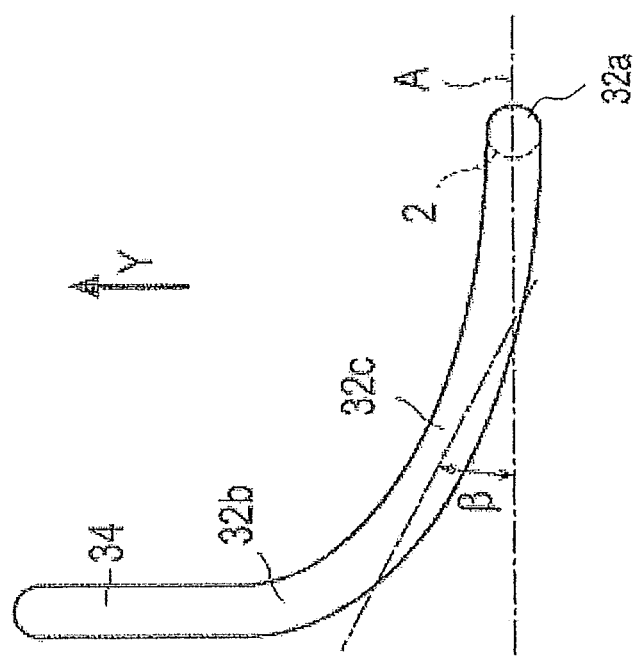
FIG. 11 is an end view of another modified example of the curved portion of the guide wire for medical treatment seen from the distal end.

Also, as shown in FIG. 11, by employing a configuration in which the inclination angle β with respect to the plane A from the curve start point 32a to the curve end point 32b becomes larger approaching the distal portion 34, it is possible to form a shape which is curved toward the Y direction moving away from the plane A. In this case, a tangent line at the curve start point 32a is on the plane A. Also, it is possible for the region curved toward the Y direction to be not only the entirety of the curved portion 32, but also a portion of the curved portion 32. Additionally, it is also possible for the bending in the Y direction to be accomplished locally or in steps/increments.

Also, although mentioned before, as shown in FIG. 12, it is possible for the most distal portion 36 of the distal portion 34 to be positioned on the side extending away from the plane B (second plane) other than on the plane C (third plane) which is parallel with the plane B and at which the curve end point 32b is positioned. Also, as shown in FIG. 13, it is possible for the most distal portion 36 of the distal portion 34 to be positioned approaching the plane B and other than on the plane C which is parallel with the plane B and at which the curve end point 32b is positioned.

In addition, it is possible for the distal section 3 to have a configuration in which the rigidity thereof is heightened appropriately by being wound with a metal wire coil or the like and it is also possible to employ a configuration of a flat plate shape formed by flattening a metal core wire. Further, depending on different purposes, it is possible to appropriately change the position at which the metal wire of coil or the like is wound or the position at which the flat plate shape is formed by pushing the metal core wire.

The guide wire disclosed here can be used for introducing a medical apparatus of a guide wire, a catheter or the like from a radial region, a brachial region and a femoral region to a target region of a chest region, an abdomen region or the like. The scope of use of the guide wire is not limited to the region at which the guide wire is introduced (the sticking region) or the target region.

The detailed description above describes features and aspects of embodiments of a guide wire and method of use. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire for use inside a medical tube comprising:
   a metal core;
   a straight proximal section possessing a distal-most end;
   a distal section possessing a proximal-most end which is continuous with the distal-most end of the proximal section so that the straight proximal section extends in a proximal direction away from the distal section;
   the distal section including a curved portion and a distal portion;
   the curved portion being a proximal-most portion of the distal section, the distal portion being located distally of the curved portion and being a distal-most part of the distal section;
   the curved portion possessing a curve start point at which curving of the curved portion starts, the curved portion possessing a curve end point at which curving of the curved portion ends, the curve start point being spaced apart from the curve end point, the curved portion curving continuously from the curve start point to the curve end point;
   the proximal section and at least a proximal-most portion of the curved portion are positioned in a common first plane, the first plane being a horizontal first plane when the straight proximal section is horizontal;
   the distal portion being oriented so that an axis of the distal portion intersects the first plane; and
   the distal portion possessing a distal-most end which is a distal-most end of the guide wire, the distal-most end of the distal portion and a distal-most part of the curved portion being located on a common side of a second plane, the second plane being perpendicular to the first plane, the straight proximal section lying in the second plane, the second plane being a vertical plane when the straight proximal section is horizontally positioned;
   wherein the distal portion and at least the distal-most part of the curved portion gradually extend away from the first plane while approaching the distal-most end of the distal portion.

2. The guide wire according to claim 1, wherein a distal-most end part of the curved portion does not lie in the first plane.

3. The guide wire according to claim 1, wherein an imaginary continuation of a distal end part of the distal portion intersects the first plane.

4. The guide wire according to claim 1, wherein an imaginary continuation of a distal end part of the distal portion intersects the first plane and the second plane.

5. The guide wire according to claim 4, wherein a distal-most end part of the curved portion does not lie in the first plane.

6. The guide wire according to claim 5, wherein the distal portion is parallel to, and spaced from, the second plane.

7. The guide wire according to claim 1, wherein the distal portion is curved so that portions of the distal portion located closer to the distal-most portion of the distal portion are spaced greater distances from the first plane.

8. A guide wire for use inside a medical tube comprising:
   a metal core;
   a proximal section possessing a distal-most end and a proximal-most end, the proximal section extending along a straight line from the distal-most end of the proximal section to the proximal-most end of the proximal section;

a distal section possessing a proximal-most end which is continuous with the distal-most end of the proximal section so that the proximal section extends in a proximal direction away from the distal section;

the distal section including a curved portion and a distal portion;

the curved portion possessing a proximal-most end that is continuous with the distal-most end of the proximal section, the curved portion also possessing a distal-most end;

the distal portion being located distally of the curved portion and possessing a proximal-most end that is continuous with the distal-most end of the curved portion;

the distal section possessing a distal-most end that is also a distal-most end of the distal portion and a distal-most end of the guide wire;

the curved portion possessing a curve start point at which curving of the curved portion starts, the curve start point coinciding with the proximal-most end of the curved portion;

the curved portion possessing a curve end point at which curving of the curved portion ends, the curve end point coinciding with the distal-most end of the curved portion;

the curve start point being spaced apart from the curve end point along a length of the curved portion, the curved portion curving continuously from the curve start point to the curve end point;

the proximal section and at least a proximal-most portion of the curved portion are positioned in a common first plane;

wherein the distal portion does not lie in the first plane; and the curved portion possessing a distal-most end part, the distal-most end part of the curved portion and the distal-most end of the distal section being positioned on a common side of a second plane, the proximal section lying in the second plane, and the second plane being perpendicular to the first plane;

wherein the distal portion and at least the distal-most part of the curved portion gradually extend away from the first plane while approaching the distal-most end of the distal portion.

9. The guide wire according to claim 8, wherein the distal-most end part of the distal portion lies in a third plane parallel to the first plane.

10. The guide wire according to claim 8, wherein the distal portion is straight.

11. The guide wire according to claim 8, wherein the distal portion is curved so that portions of the distal portion located closer to the distal-most end of the distal section are greater distances from the first plane.

12. A guide wire for use inside a medical tube comprising:
a metal core;
a straight-line shaped proximal section;
a distal section continuous with a distal end of the proximal section so that a distal-most portion of the distal section faces in a proximal direction;
the distal section including a curved portion continuous with the proximal section and a distal portion continuous with a distal end of the curved portion;
the proximal section and at least a proximal portion of the curved portion which is continuous with the proximal section being positioned on a common first plane;
the distal portion extending toward a direction directed away from the first plane, the distal portion including a distal-most end;
the distal-most end of the distal portion being positioned on one side of a second plane which is orthogonal to the first plane and in which the proximal section lies; and
at least a distal portion of the curved portion being positioned on said one side of the second plane;
wherein the distal portion and at least the distal-most part of the curved portion gradually extend away from the first plane while approaching the distal-most end of the distal portion.

13. The guide wire according to claim 12, wherein at least a distal-most part of the curved portion extends away from the first plane.

14. The guide wire according to claim 12, wherein at least a distal-most part of the curved portion extends away from the first plane and lies in a plane different from the first plane.

15. The guide wire according to claim 12, wherein the distal portion is straight and inclined at an inclination angle with respect to the first plane.

16. The guide wire according to claim 12, wherein the distal portion is straight and forms an acute angle with the first plane, the acute angle being greater than zero degrees.

17. The guide wire according to claim 16, wherein the distal portion is parallel to, and spaced from, the second plane.

18. The guide wire according to claim 12, wherein the distal portion is curved so that portions of the distal portion located closer to the distal-most portion are greater distances from the first plane.

19. The guide wire according to claim 1, wherein said metal core is a solid metal core.

20. The guide wire according to claim 8, wherein said metal core is a solid metal core.

21. The guide wire according to claim 12, wherein said metal core is a solid metal core.

* * * * *